(12) United States Patent
Jung

(10) Patent No.: US 12,158,413 B2
(45) Date of Patent: Dec. 3, 2024

(54) FOOD ANALYSIS APPARATUS

(71) Applicant: BEYOND HONEYCOMB INC, Busan (KR)

(72) Inventor: Hyun Ki Jung, Seoul (KR)

(73) Assignee: BEYOND HONEYCOMB INC, Busan (KR)

( * ) Notice: Subject to any disclaimer, the term of this patent is extended or adjusted under 35 U.S.C. 154(b) by 0 days.

(21) Appl. No.: 17/768,318

(22) PCT Filed: Jan. 20, 2022

(86) PCT No.: PCT/KR2022/001069
§ 371 (c)(1),
(2) Date: Apr. 12, 2022

(87) PCT Pub. No.: WO2022/186481
PCT Pub. Date: Sep. 9, 2022

(65) Prior Publication Data
US 2024/0102920 A1 Mar. 28, 2024

(30) Foreign Application Priority Data

Mar. 2, 2021 (KR) .................. 10-2021-0027588

(51) Int. Cl.
G01N 21/25 (2006.01)
F24C 3/12 (2006.01)
F24C 7/08 (2006.01)
F24C 15/00 (2006.01)
G01N 21/27 (2006.01)
G01N 33/02 (2006.01)

(52) U.S. Cl.
CPC ........... *G01N 21/255* (2013.01); *F24C 3/128* (2013.01); *F24C 7/085* (2013.01); *F24C 15/00* (2013.01); *G01N 21/27* (2013.01); *G01N 33/02* (2013.01); *G01N 2201/021* (2013.01)

(58) Field of Classification Search
CPC ...... G01N 21/255; G01N 21/27; G01N 33/02; F24C 3/128; F24C 7/085; F24C 15/00
USPC ........................................................ 126/237
See application file for complete search history.

(56) References Cited

U.S. PATENT DOCUMENTS

2017/0184453 A1* 6/2017 Wang ..................... G01J 3/021
2018/0172510 A1* 6/2018 Rosen .................. G01J 3/0205
2018/0284091 A1* 10/2018 Levanon ................ G01K 13/10

FOREIGN PATENT DOCUMENTS

| KR | 1999-0051985 A | 7/1999 |
| KR | 10-2010-0042544 A | 4/2010 |
| KR | 10-2016-0092888 A | 8/2016 |
| KR | 10-2019-0038184 A | 4/2019 |

* cited by examiner

Primary Examiner — Vivek K Shirsat
(74) Attorney, Agent, or Firm — Sughrue Mion, PLLC

(57) ABSTRACT

The present invention relates to a food analysis apparatus including a cooking chamber provided in a cooking appliance, a measuring unit mounted in the cooking chamber and configured to irradiate food placed in a cooking region inside the cooking chamber with light and then sense spectral characteristics of reflected light, and an analyzing unit configured to analyze the spectral characteristics transmitted from the measuring unit to detect molecular information of the food.

17 Claims, 14 Drawing Sheets

[FIG .1]
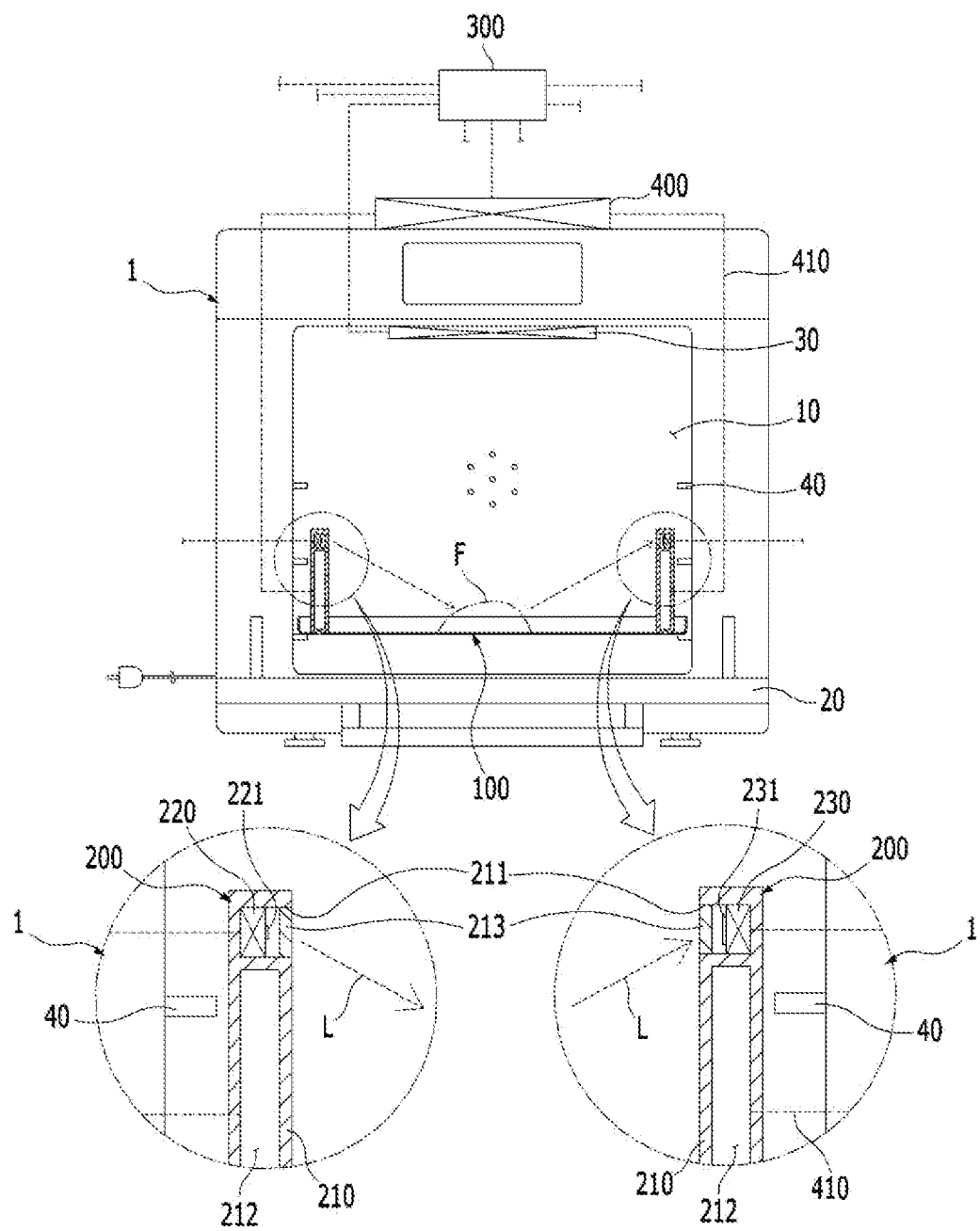

[FIG .2]
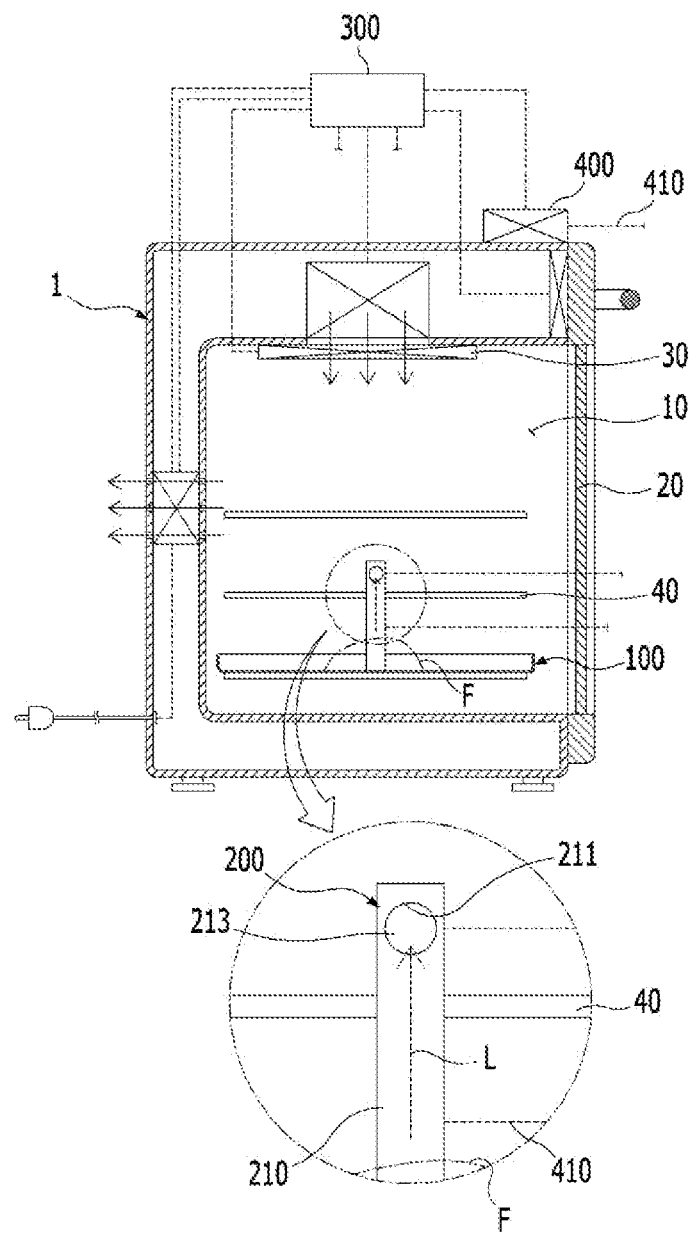

[FIG .3]
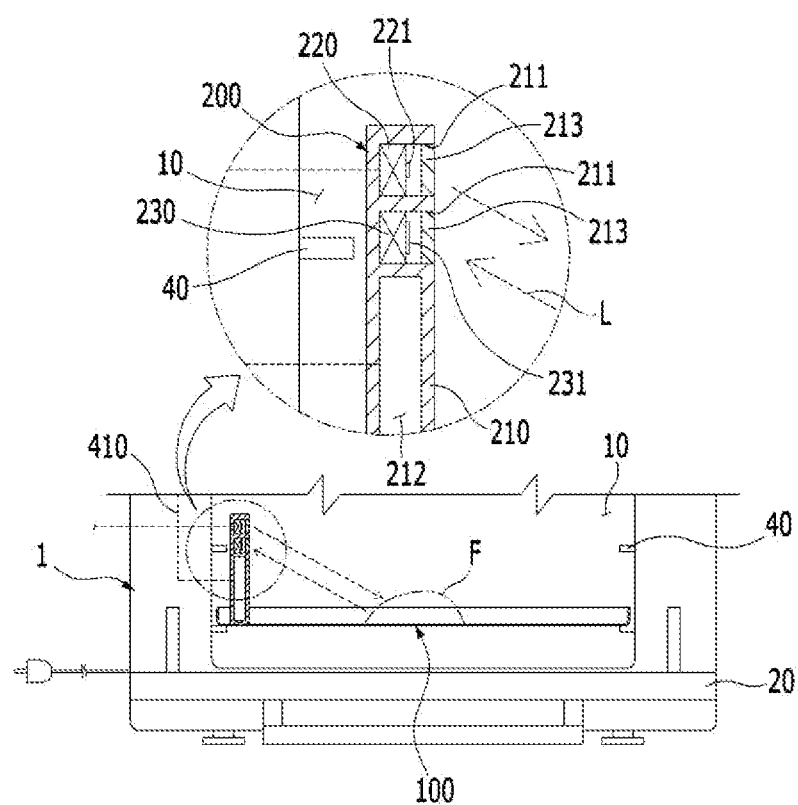

[FIG .4]
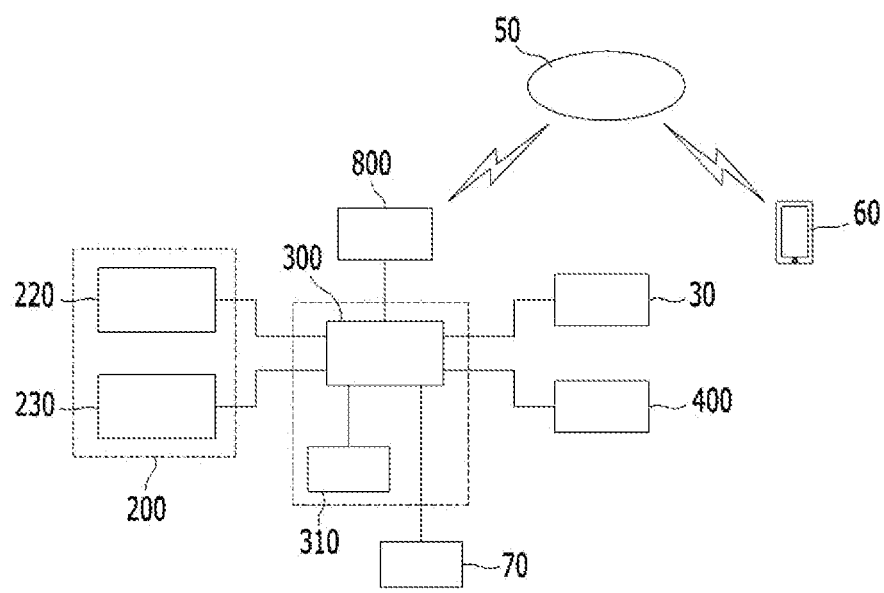

[FIG .5]
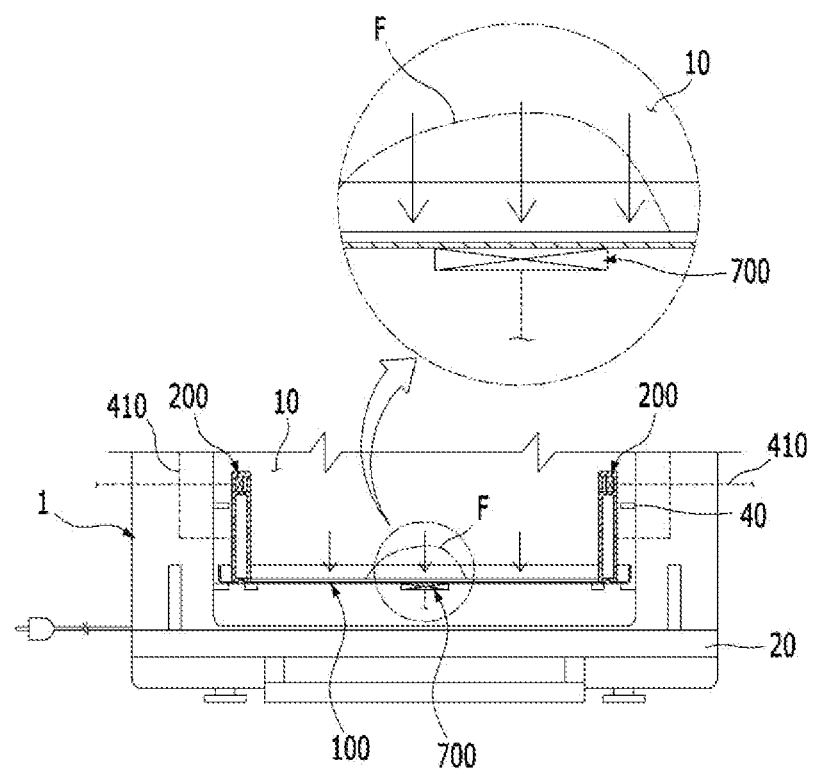

[FIG .6]
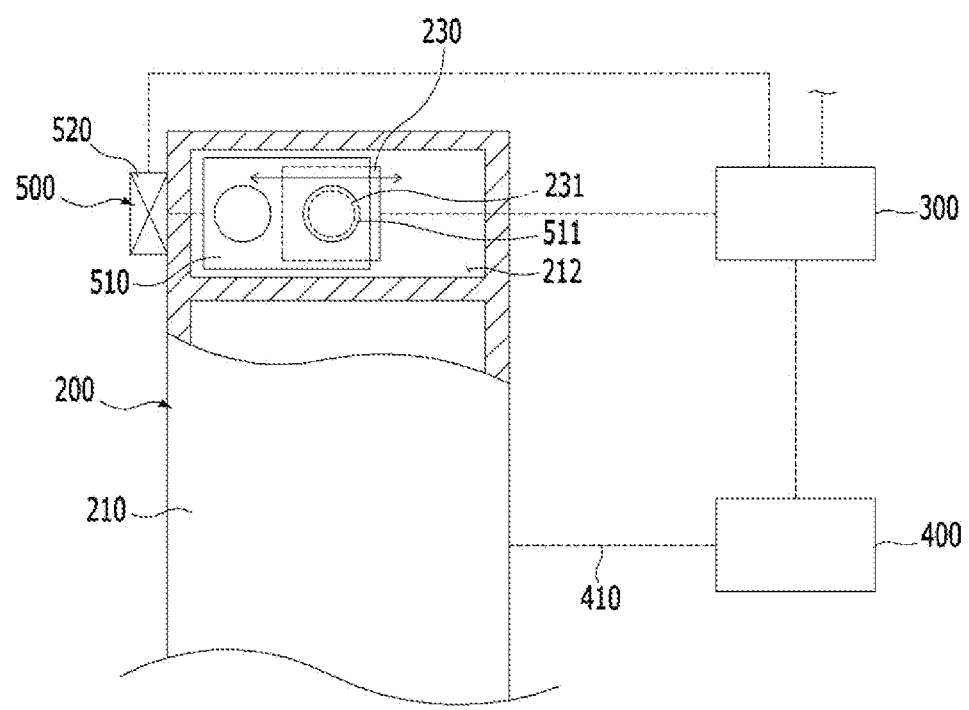

[FIG .7]
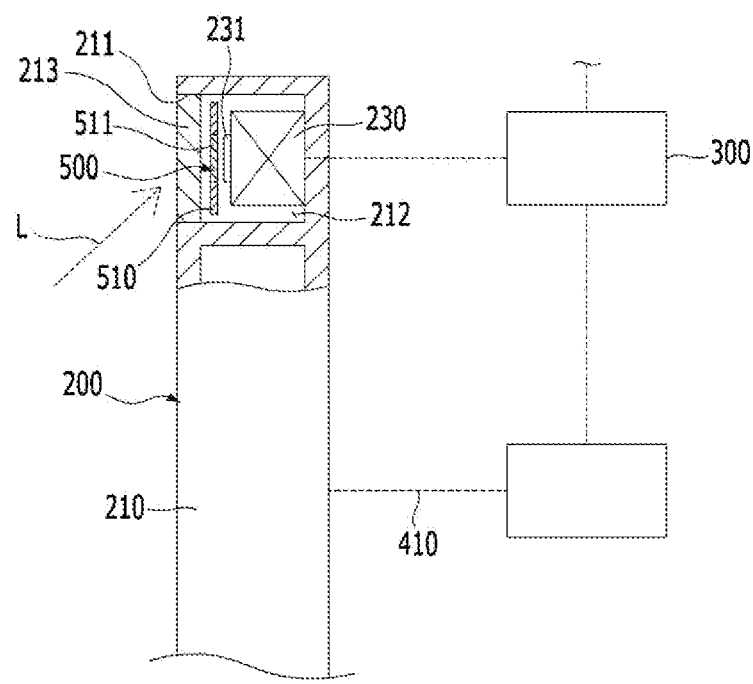

[FIG .8]
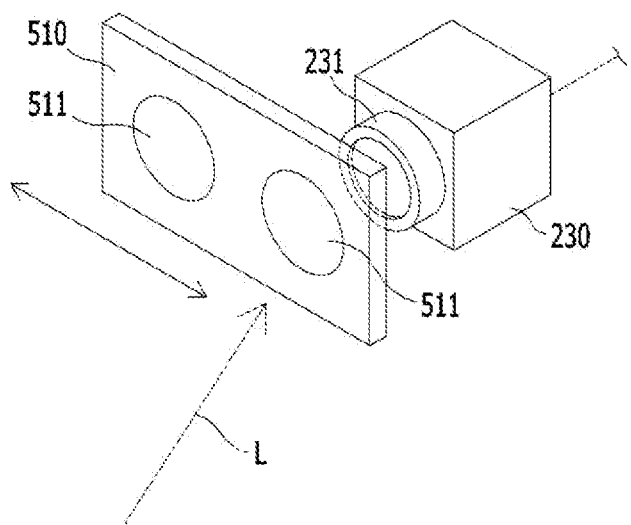

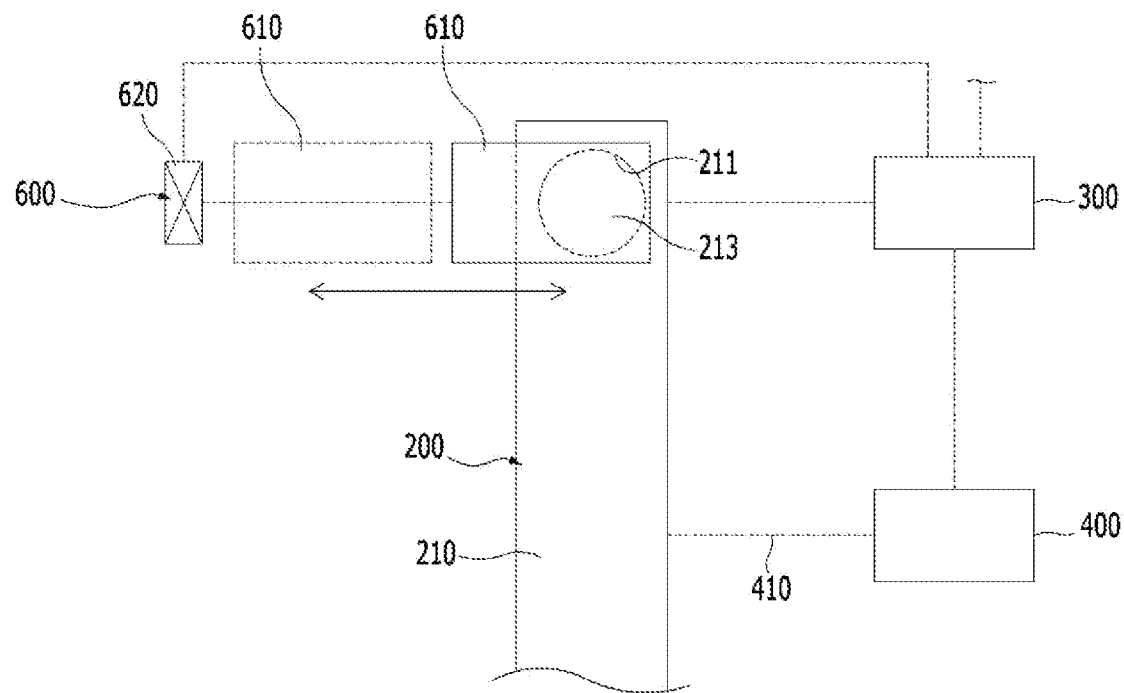
[FIG .9]

[FIG .10]
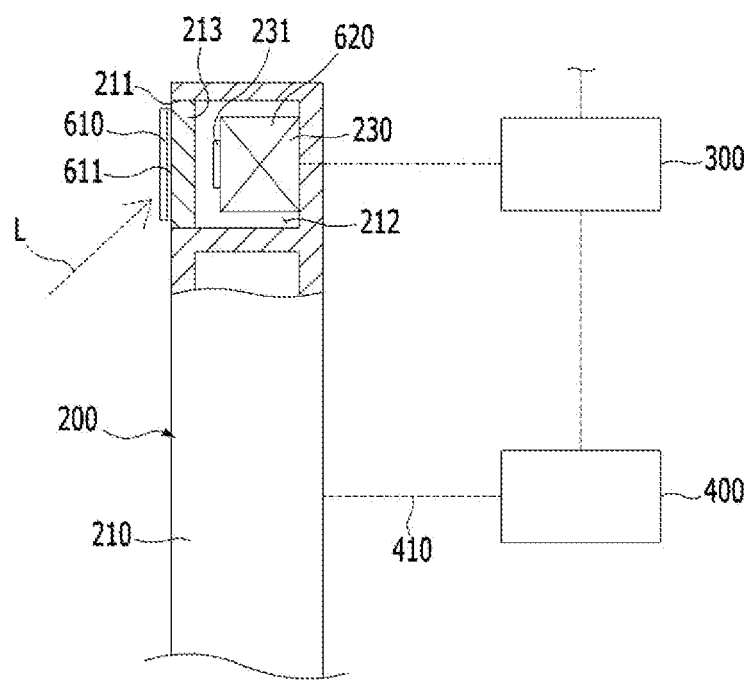

[FIG .11]
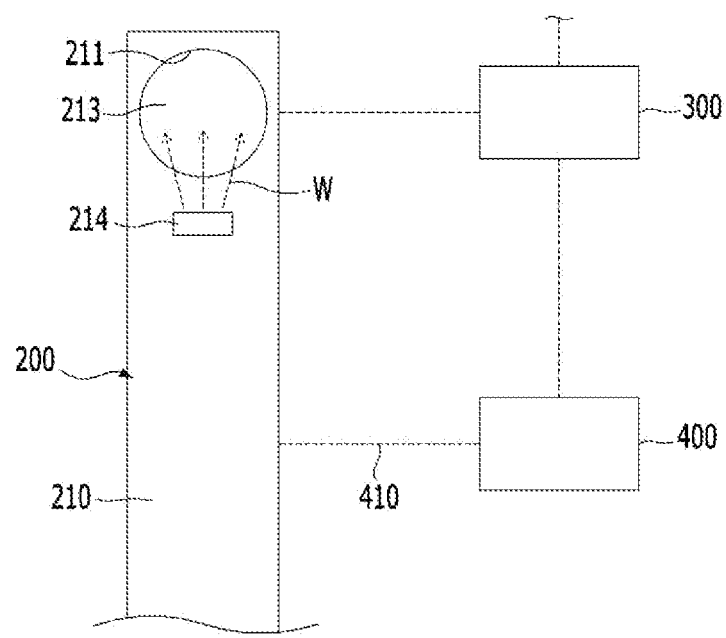

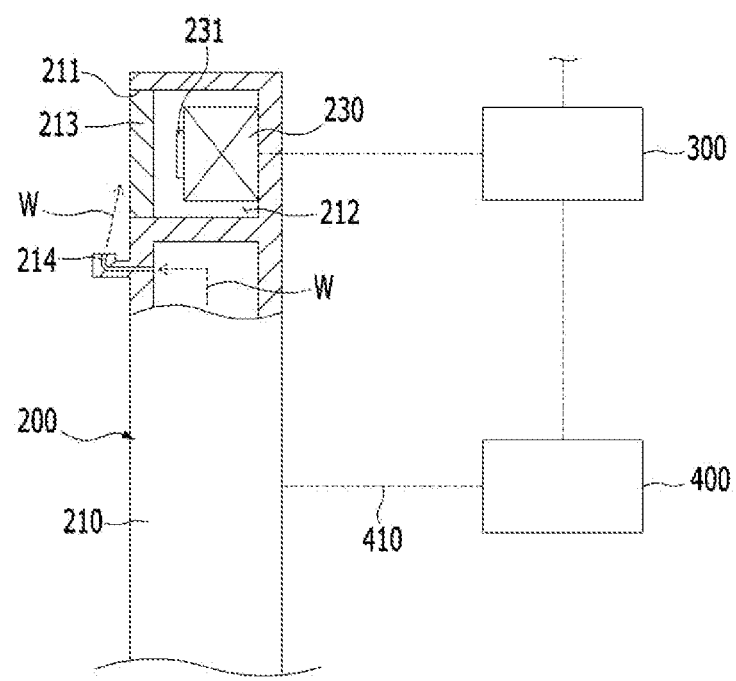
[FIG .12]

[FIG .13]
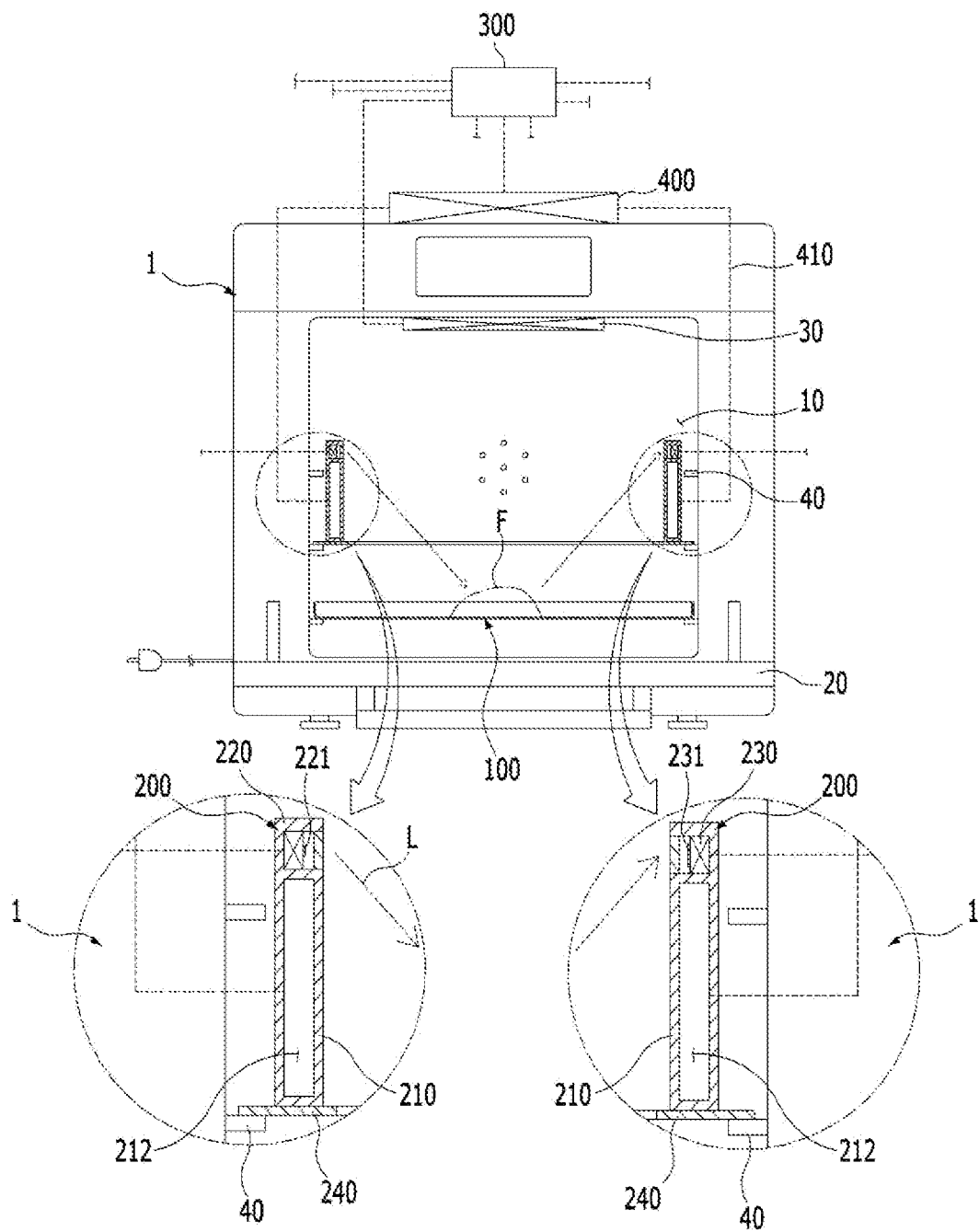

[FIG .14]
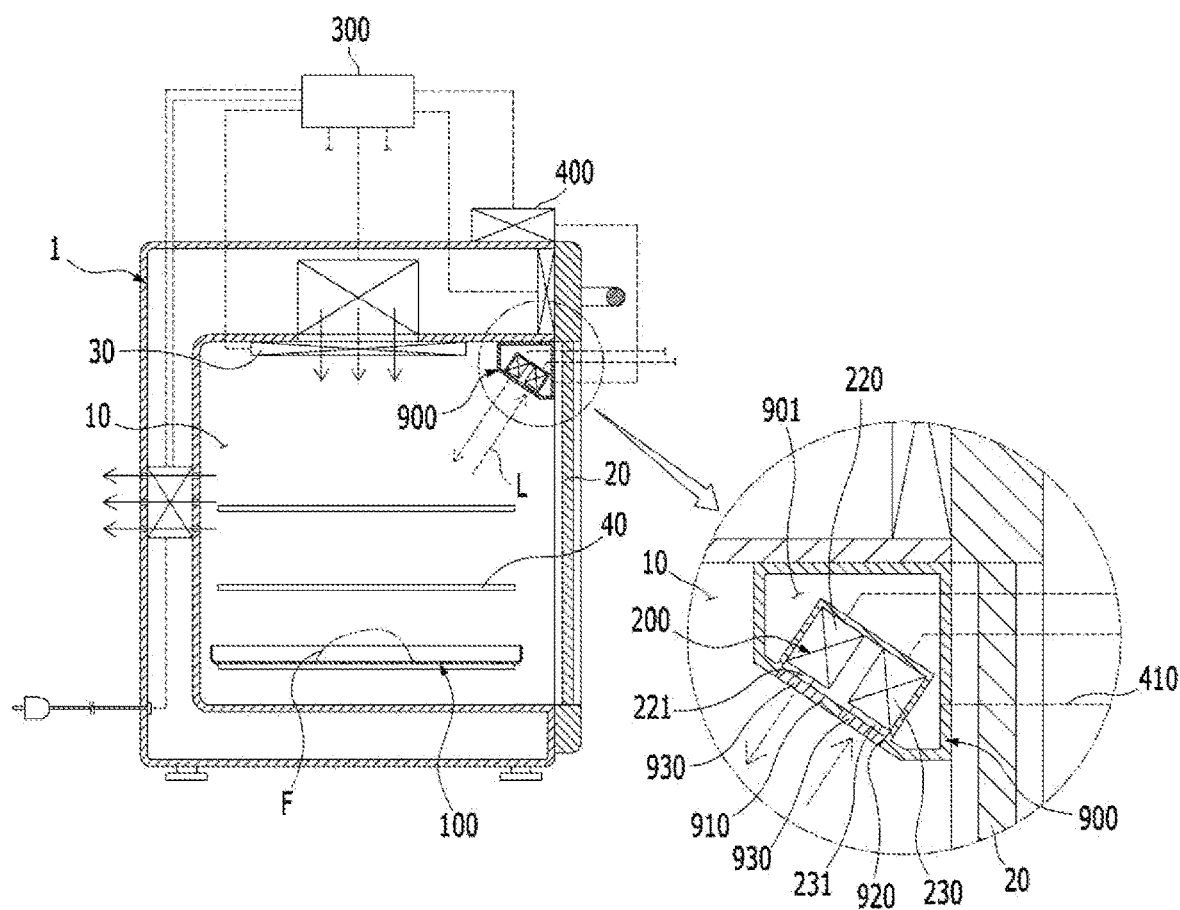

FOOD ANALYSIS APPARATUS

CROSS REFERENCE TO RELATED APPLICATIONS

This application is a National Stage of International Application No. PCT/KR2022/001069 filed Jan. 20, 2022, claiming priority based on Korean Patent Application No. 10-2021-0027588 filed Mar. 2, 2021, the entire disclosures of which are incorporated herein by reference.

TECHNICAL FIELD

The present invention relates to a food analysis apparatus, and more particularly, to a food analysis apparatus capable of analyzing molecular information of food in a cooking process.

BACKGROUND ART

Generally, ovens are appliances for cooking food by applying heat to it and consist of a main body in which a cooking chamber is provided, a heating part configured to apply heat to the cooking chamber, an air blowing part configured to circulate the heat generated by the heating part throughout the inside of the cooking chamber, a door for opening/closing the cooking chamber, and the like.

Such ovens are classified into an electric type, a gas type, an electronic type, etc. according to the type of heat source used. Electric ovens use an electric heater as a heat source, and gas ovens and electronic ovens use heat from gas and the frictional heat of high frequency water molecules, respectively, as heat sources.

In recent years, a technology in which an optical device (a camera or the like) is installed inside an oven to capture an image of the inside of a cooking chamber has been disclosed. An oven using an optical device allows, by use of the optical device, a cooking state of food to be monitored through a smart device or the oven to be remotely controlled by a user to make it convenient for the user to use the oven.

In the conventional oven using an optical device, a heating part for applying heat to food is installed at an upper portion of a cooking chamber, and the optical device for capturing an image of the food placed in the cooking chamber is installed at the upper portion of the cooking chamber. Also, a heat-resistant member (heat-resistant glass or the like) for minimizing the influence of heat is installed at a lens portion of the optical device, and a cooling fan or the like for cooling the optical device is installed at the upper portion of the cooking chamber.

However, in the conventional oven using the optical device, since the heating part and the optical device are located at the upper portion of the cooking chamber, oil mist, smoke, steam, and the like generated during a cooking process may be attached to the lens of the optical device, and thus there is a concern of causing degradation of the sensing performance of the optical device.

Also, in the conventional oven using the optical device, since the optical device is installed at a position adjacent to the heating part, there is a risk of burns in the process of cleaning the lens of the optical device, and since the structure of the heating part should be changed to secure an image capturing region of the optical device, there is a concern of causing degradation of the heating performance of the heating part.

DISCLOSURE

Technical Problem

The present invention is directed to providing a food analysis apparatus capable of analyzing molecular information of food in a cooking process.

Technical Solution

One aspect of the present invention provides a food analysis apparatus including a cooking chamber provided in a cooking appliance, a measuring unit configured to irradiate food placed in a cooking region inside the cooking chamber with light and then sense spectral characteristics of reflected light, and an analyzing unit configured to analyze the spectral characteristics transmitted from the measuring unit to detect the molecular information of the food.

Also, the food analysis apparatus may further include a tray which is mounted in the cooking chamber and has the cooking region formed at an upper portion, and the measuring unit may be provided at the upper portion of the tray.

Also, the food analysis apparatus may further include a mounting frame which is mounted in the cooking chamber and has a hollow vertically passing therethrough, and the measuring unit may be provided on the mounting frame.

Also, the measuring unit may include a support part which has a pair of through-holes provided at one side, a light emitting part which is provided in the support part and configured to irradiate the food placed in the cooking region with light through one of the pair of through-holes, and a light receiving part which is provided in the support part and configured to sense spectral characteristics of light that is incident through the other one of the pair of through-holes and transmit the spectral characteristics to the analyzing unit.

Also, the measuring unit may include a pair of support parts each having a through-hole formed at one side, a light emitting part which is provided in one of the pair of support parts and configured to irradiate the food placed in the cooking region with light through the through-hole, and a light receiving part which is provided in the other one of the pair of support parts and configured to sense spectral characteristics of light that is incident through the through-hole and transmit the spectral characteristics to the analyzing unit.

Also, the food analysis apparatus may further include a filter unit configured to selectively block light of a wavelength in a specific range that is incident on the light receiving part, and the filter unit may further include a first moving part which is provided to be position-changeable in front of the light receiving part and has one or more noise filters provided in front of the light receiving part or provided to avoid the front of the light receiving part and a first driving part which is electrically connected to the analyzing unit and configured to change the position of the first moving part.

Also, a heat-resistant member for passing light and blocking heat may be further coupled to the through-hole.

Also, the food analysis apparatus may further include a power supply unit electrically connected to the measuring unit and a cooling unit for circulating a refrigerant throughout the inside of the support part.

Also, the food analysis apparatus may further include a refrigerant discharging part which is formed to be penetrated at an outer portion of the support part and allows the refrigerant to be sprayed to an outer surface of the heat-resistant member.

Also, the food analysis apparatus may further include a cover unit provided to be position-changeable at one side of the support part, and the cover unit may further include a second moving part which is provided to be movable between a position for covering the outer surface of the heat-resistant member and a position for exposing the outer surface of the heat-resistant member and a second driving part which is electrically connected to the analyzing unit and configured to change the position of the second moving part.

Also, the food analysis apparatus may further include a weight sensing unit which is provided at the upper portion of the tray and configured to measure the weight of the food placed in the cooking region, and the weight sensing unit may be electrically connected to the analyzing unit and transmit the measured weight of the food to the analyzing unit.

Also, the analyzing unit may display the cooking state of the food to the outside.

Also, the analyzing unit may automatically control operation of the cooking appliance according to the detected molecular information.

Also, the food analysis apparatus may further include an adjuster for controlling the operation of the cooking appliance and a robot controller which is mechanically connected to the adjuster and configured to manipulate the adjuster by operation control of the analyzing unit, and the analyzing unit may automatically control operation of the robot controller.

Also, the analyzing unit may control the cooking appliance by a wired or wireless communication method.

Another aspect of the present invention provides a food analysis apparatus including a cooking chamber which is provided in a cooking appliance and has an installation region provided at an upper end of one side, a measuring unit which is coupled to the installation region and configured to irradiate light to be inclined downward toward food placed in the cooking chamber and then sense spectral characteristics of reflected light, and an analyzing unit which is electrically connected to the measuring unit and configured to analyze the spectral characteristics transmitted from the measuring unit to detect molecular information of the food.

Also, the measuring unit may include a housing which is coupled to the installation region and has a sensing surface formed to be inclined downward at one side, a first through-hole provided to be inclined downward in the sensing surface, a second through-hole provided to be inclined downward in the sensing surface, a light emitting part which is provided in the housing and configured to irradiate light to be inclined downward toward the food through the first through-hole, and a light receiving part which is provided in the housing and configured to sense spectral characteristics of light that is incident to be inclined upward through the second through-hole.

Also, the food analysis apparatus may further include a power supply unit electrically connected to the measuring unit and a cooling unit configured to circulate a refrigerant throughout the inside of the housing.

Advantageous Effects

According to the present invention, since it is possible to analyze molecular information of food in real time in a cooking process, the corresponding food can be cooked with an optimal recipe, and since a measuring unit is located at a position spaced apart from an installation region of a heating part, the measuring unit can be easily cleaned without interference between the measuring unit and the heating part, and the risk of accidents while cleaning the measuring unit can be reduced.

Also, according to the present invention, since it is easy to secure an installation space for the heating part, degradation of heating performance can be prevented. Since application to various cooking appliances is possible, a general-purpose use is possible. Since it is possible to prevent attachment of foreign matter to the measuring unit and remove foreign matter attached to the measuring unit during the cooking process, food analysis performance can be maintained in an optimal state.

DESCRIPTION OF DRAWINGS

FIG. 1 is a front view showing a food analysis apparatus according to one embodiment of the present invention.

FIG. 2 is a lateral cross-sectional view showing the food analysis apparatus according to one embodiment of the present invention.

FIG. 3 is a front view showing a state in which a light emitting part and a light receiving part are installed together in a support rack of the food analysis apparatus according to one embodiment of the present invention.

FIG. 4 is a block diagram schematically showing the connection relationship between components of the food analysis apparatus according to one embodiment of the present invention.

FIG. 5 is a front view showing a weight sensing unit of the food analysis apparatus according to one embodiment of the present invention.

FIG. 6 is a front cross-sectional view showing a filter unit of the food analysis apparatus according to one embodiment of the present invention.

FIG. 7 is a lateral cross-sectional view showing the filter unit of the food analysis apparatus according to one embodiment of the present invention.

FIG. 8 is a perspective view showing the filter unit of the food analysis apparatus according to one embodiment of the present invention.

FIG. 9 is a front view showing a cover unit of the food analysis apparatus according to one embodiment of the present invention.

FIG. 10 is a lateral cross-sectional view showing the cover unit of the food analysis apparatus according to one embodiment of the present invention.

FIG. 11 is a front view showing a refrigerant discharging part of the food analysis apparatus according to one embodiment of the present invention.

FIG. 12 is a lateral cross-sectional view showing the refrigerant discharging part of the food analysis apparatus according to one embodiment of the present invention.

FIG. 13 is a lateral cross-sectional view showing a state in which a mounting frame is applied to a cooking chamber of the food analysis apparatus according to one embodiment of the present invention.

FIG. 14 is a lateral cross-sectional view showing a food analysis apparatus according to another embodiment of the present invention.

BEST MODE OF THE INVENTION

Hereinafter, exemplary embodiments according to the present invention will be described in detail with reference to the accompanying drawings.

Advantages and features of the present invention and a method of achieving the same should become clear with embodiments described in detail below with reference to the accompanying drawings.

However, the present invention is not limited to embodiments disclosed below and is realized in various different forms. The present embodiments make the disclosure of the present invention complete and are provided to completely inform one of ordinary skill in the art to which the present invention pertains of the scope of the disclosure. The present invention is defined only by the scope of the claims.

In addition, in describing the present invention, when detailed description of a known related art is considered as having the possibility of obscuring the gist of the present invention, the detailed description thereof will be omitted.

FIG. 1 is a front view showing a food analysis apparatus according to one embodiment of the present invention, FIG. 2 is a lateral cross-sectional view showing the food analysis apparatus according to one embodiment of the present invention, and FIG. 3 is a front view showing a state in which a light emitting part and a light receiving part are installed together in a support rack of the food analysis apparatus according to one embodiment of the present invention.

FIG. 4 is a block diagram schematically showing the connection relationship between components of the food analysis apparatus according to one embodiment of the present invention, FIG. 5 is a front view showing a weight sensing unit of the food analysis apparatus according to one embodiment of the present invention, and FIG. 6 is a front cross-sectional view showing a filter unit of the food analysis apparatus according to one embodiment of the present invention.

FIG. 7 is a lateral cross-sectional view showing the filter unit of the food analysis apparatus according to one embodiment of the present invention, FIG. 8 is a perspective view showing the filter unit of the food analysis apparatus according to one embodiment of the present invention, and FIG. 9 is a front view showing a cover unit of the food analysis apparatus according to one embodiment of the present invention.

FIG. 10 is a lateral cross-sectional view showing the cover unit of the food analysis apparatus according to one embodiment of the present invention, and FIG. 11 is a front view showing a refrigerant discharging part of the food analysis apparatus according to one embodiment of the present invention. Also, FIG. 12 is a lateral cross-sectional view showing the refrigerant discharging part of the food analysis apparatus according to one embodiment of the present invention, and FIG. 13 is a lateral cross-sectional view showing a state in which a mounting frame is applied to a cooking chamber of the food analysis apparatus according to one embodiment of the present invention. FIG. 14 is a lateral cross-sectional view showing a food analysis apparatus according to another embodiment of the present invention.

Referring to FIGS. 1 to 13, a food analysis apparatus according to one embodiment of the present invention includes a cooking chamber 10 of a cooking appliance 1 (an oven or the like), a tray 100, a measuring unit 200, and an analyzing unit 300.

The cooking chamber 10 forms a cooking space of a certain area so that food F may be placed therein, and a door part 20 is provided to be openable/closeable at one side (front or the like) of the cooking chamber 10. The door part 20 may have a handle provided to be gripped by a user's hand and may have a transparent display window provided to allow the user to check the inside of the cooking chamber 10 by visual inspection.

Also, a heating part 30 for applying heat to the food F may be provided at an upper portion of the cooking chamber 10, the heating part 30 may have a structure that is heated by power transmitted from the outside, and an air blowing part for blowing heated air toward the cooking chamber 10 may be provided at an upper portion of the heating part 30.

In addition, a discharge part for discharging air to the outside may be provided at one side of the cooking chamber 10, an air blowing part for discharging an odor or the like generated during cooking to the outside may be provided in the discharge part, and a lighting part may be provided inside the cooking chamber 10 to be turned on in an operational situation such as when cooking is performed or when opening of the door part 20 is sensed.

Further, a mounting part 40 for placing the tray 100 at a certain height may be provided at both sides of the cooking chamber 10. A plurality of mounting parts 40 may be arranged in a state of being spaced apart from each other in the vertical direction to allow a height for mounting the tray 100 to be selected.

The tray 100 is mounted in the cooking chamber 10. The tray 100 has a cooking region of a certain area formed at an upper portion so that the food F may be placed thereon, and a metal (stainless steel, etc.) or the like may be used as a material of the tray 100 to prevent the tray 100 from being deformed by certain heat.

The tray 100 may be horizontally mounted in the cooking chamber 10 in a state in which the food F is seated on the cooking region at the upper portion, and lower ends of both sides of the tray 100 may be mounted in a state of being seated on upper ends of the mounting parts 40 or may be mounted in a state of being seated on a mesh (not illustrated) or the like that is seated on the mounting part 40.

In the food analysis apparatus according to one embodiment of the present invention, as in FIG. 13, a mounting frame 240 may be installed inside the cooking chamber 10. In this case, the measuring unit 200 may be installed at an upper portion of the mounting frame 240.

The mounting frame 240 may have a hollow vertically passing therethrough to allow light L to pass, lower ends of both sides of the mounting frame 240 may be mounted in a state of being seated on the upper ends of the mounting parts 40, and the measuring unit 200, which will be described below, may be installed at the upper portion of the mounting frame 240.

The measuring unit 200 is for irradiating the food F placed in the cooking region at the lower portion inside the cooking chamber 10 with the light L and then receiving the reflected light L to sense spectral characteristics thereof. The measuring unit 200 may be installed at an upper portion of the tray 100 but may be installed to be fixed in the cooking chamber 10 as necessary.

In the case where the measuring unit 200 is installed at the upper portion of the mounting frame 240, as in FIG. 13, the measuring unit 200 may irradiate the food F placed in the cooking region with the light L through the hollow of the mounting frame 240 and then receive the reflected light L to sense spectral characteristics thereof.

As in FIG. 1, the measuring unit 200 according to one embodiment of the present invention may include a pair of support parts 210 each having a through-hole 211 formed at one side, a light emitting part 220 which is provided in one of the pair of support parts 210 and configured to irradiate the light L to be inclined downward toward the food, which is placed in the cooking region, through the through-hole 211, and a light receiving part 230 which is provided in the other one of the pair of support parts 210 and configured to sense spectral characteristics of the light L that is incident through the through-hole 211 and transmit the spectral characteristics to the analyzing unit 300.

The pair of support parts 210 may be located to correspond to both side directions (along an upper surface, an edge-side end portion, etc.) of the tray 100 or both side directions (along an upper surface, an edge-side end portion, etc.) of the mounting frame 240 with respect to the cooking region. The through-holes 211 may be formed to correspond to each other at one side of the support part 210 and one side of the other support part 210 that face each other, and an installation space 212 for installing the light emitting part 220 or the light receiving part 230 may be formed in each of the support parts 210.

Also, the support part 210 may have a length in the vertical direction, a lower end of the support part 210 may be coupled to be fixed to the upper portion of the tray 100 or the upper portion of the mounting frame 240, and the support part 210 may be manufactured using a heat-resistant material to prevent the support part 210 from being deformed by heat transmitted from the outside during cooking.

In another form, the lower end of each support part 210 may be applied to be couplable to and separable from the upper portion of the tray 100. In this case, the lower end of the support part 210 and the upper surface of the tray 100 may be coupled by a male-female coupling structure (using a protrusion, a groove, etc.), or the lower end of the support part 210 and the upper surface of the tray 100 may be coupled to and separated from each other by a screw coupling method.

Meanwhile, the lower end of each support part 210 may be applied to be couplable to and separable from the upper surface of the mounting frame 240. In this case, the lower end of the support part 210 and the upper surface of the mounting frame 240 may be coupled by a male-female coupling structure (using a protrusion, a groove, etc.), or the lower end of the support part 210 and the upper surface of the mounting frame 240 may be coupled to and separated from each other by a screw coupling method.

Also, a heat-resistant member 213 for passing the light L and blocking heat may be further coupled to the through-hole 211 of each support part 210. The heat-resistant member 213 may be manufactured using a heat-resistant material to prevent the heat-resistant member 213 from being deformed by heat transmitted from the outside during cooking, or various other materials may be selectively used as necessary for the heat-resistant member 213.

The light emitting part 220 is a component for irradiating the food F seated on the cooking region of the tray 100 with the light L. The light emitting part 220 may be installed in the installation space 212 of any one of the pair of support parts 210, and the light emitting part 220 may be electrically connected (via a wire or wirelessly) to the analyzing unit 300, which will be described below, for operation of the light emitting part 220 to be controlled.

Here, one or more lamps 221 for irradiating the light L to be inclined downward toward the cooking region of the tray 100 through the through-hole 211 may be installed at one side of the light emitting part 220. A light emitting diode (LED) may be used for the lamp 221, but various other forms may be selectively used as necessary for the lamp 221.

The light L irradiated from the lamp 221 of the light emitting part 220 may be irradiated to be inclined downward toward the food F placed in the cooking region of the tray 100 through the heat-resistant member 213, and the light L reflected from the food F may be incident to be inclined upward through the light receiving part 230 which will be described below.

Here, the light L irradiated from the lamp 221 of the light emitting part 220 may be irradiated with a certain area toward the cooking region, and the area, angle, illuminance, or the like with which the light L is irradiated may vary according to the size and installation conditions (position, height, etc.) of the tray 100. The light L irradiated from the lamp 221 may be irradiated toward the entire region of the cooking region or irradiated toward a partial region of the cooking region.

The light receiving part 230 is a component for receiving the light L reflected from the food F. The light receiving part 230 may be installed in the installation space 212 of the support part 210 that corresponds to the support part 210 in which the light emitting part 220 is installed, and the light receiving part 230 may be electrically connected (via a wire or wirelessly) to the analyzing unit 300, which will be described below, for operation of the light receiving part 230 to be controlled.

Here, a lens 231 for receiving the light L incident through the through-hole 211 may be installed at one side of the light receiving part 230. An image sensor such as a complementary metal-oxide semiconductor (CMOS) or a charge-coupled device (CCD) may be selectively used for the light receiving part 230, but various other sensing methods may be used as necessary for the light receiving part 230.

In the case where the light L reflected from the food F is received through the lens 231, the light receiving part 230 senses spectral characteristics of the received light and transmits a sensing signal to the analyzing unit 300 which will be described below. Here, the analyzing unit 300 analyzes the spectral characteristics transmitted from the light receiving part 230 to detect molecular information of the food F.

Meanwhile, the light emitting part 220 and the light receiving part 230 of the present invention may be installed together in a single support part 210 as in FIG. 3. In this case, the support part 210 may be located in one side direction (along the upper surface, the edge-side end portion, etc.) of the tray 100 or one side direction (along the upper surface, the edge-side end portion, etc.) of the mounting frame 240 with respect to the cooking region. The light emitting part 220 and the light receiving part 230 may be installed together in the installation space 212 of the support part 210, and the through-hole 211 may be formed at one side of the support part 210 to allow passage of the light L.

Also, each of the through-hole 211 for passing the light L irradiated from the lamp 221 of the light emitting part 220 and the through-hole 211 for passing the light received through the lens 231 of the light receiving part 230 may be formed at one side of the support part 210. In another form, a single through-hole 211 may be formed to pass the light L irradiated from the lamp 221 and the light L received through the lens 231 together.

For example, the light emitting part 220 and the light receiving part 230 may be installed in vertical and horizontal directions of the installation space 212, and the through-hole 211 may be installed at a height that corresponds to one side of the light emitting part 220 and the light receiving part 230. The installation positions of the light emitting part 220, the light receiving part 230, and the through-hole 211 may be changed in various ways as necessary.

Further, the heat-resistant member 213 for passing the light L and blocking heat may be further coupled to the through-hole 211. The heat-resistant member 213 may be manufactured using a heat-resistant material to prevent the heat-resistant member 213 from being deformed by heat transmitted from the outside during cooking, or various other materials may be selectively used as necessary for the heat-resistant member 213.

The analyzing unit 300 may analyze the spectral characteristics of the light L, which are transmitted from the measuring unit 200, to detect molecular information (moisture content, a protein/fat/collagen composition ratio, the degree of ripening, the degree of Maillard reaction, a change in characteristics of muscle fibers, etc.) of the food F and may control operation of the heating part 30 of the cooking appliance 1, the air blowing part, the measuring unit 200, and the like.

Here, the analyzing unit 300 may be located outside the cooking appliance 1 or installed in a state of being coupled to the cooking appliance 1, and a power supply unit 70 for supplying power and a manipulation part 310 configured to allow manipulation by the user may be electrically connected to the analyzing unit 300.

Also, the analyzing unit 300 may be electrically connected to the light emitting part 220 and the light receiving part 230 by a power cable, the power cable connected to the analyzing unit 300 may be connected to each of the light emitting part 220 and the light receiving part 230 through the inside of the support parts 210, and the manipulation part 310 may be connected via a wire or wirelessly to the analyzing unit 300.

In the case where a wired manipulation method is applied to the manipulation part 310, the manipulation part 310 and the analyzing unit 300 may be connected by a connection line (a cable, etc.). In this case, the manipulation part 310 may be installed in a state of being coupled to an outer portion of the cooking appliance 1 or installed in a state of being connected to the cooking appliance 1 by the connection line.

On the other hand, in the case where a wireless manipulation method is applied to the manipulation part 310, a near-field communication method such as radio frequency identification (RFID), Bluetooth, and Wi-Fi may be used for connecting the manipulation part 310 and the analyzing unit 300.

Also, a manipulation switch (not illustrated) for allowing the user to control the operation of the cooking appliance 1 and a display part (not illustrated) for displaying various pieces of information (cooking time, cooking intensity, molecular information, etc.) of the cooking appliance 1 to the outside may be provided at the manipulation part 310, and in the case where a wireless manipulation method is applied to the manipulation part 310, a battery module (not illustrated) which is replaceable or rechargeable may be provided in the manipulation part 310.

In addition, the analyzing unit 300 may detect molecular information (moisture content, a protein/fat/collagen composition ratio, the degree of ripening, the degree of Maillard reaction, a change in characteristics of muscle fibers, etc.) of the food F and display a cooking state of the food F to the outside in a process in which the cooking appliance 1 operates, and using the analyzed molecular information, the analyzing unit 300 may automatically cook the corresponding food F with a set recipe.

Further, an automatic cooking program (time, temperature, etc.) of the food F may be preset in the analyzing unit 300. In this case, the analyzing unit 300 may automatically control the operation of the cooking appliance 1 using the automatic cooking program according to the detected molecular information. That is, using the automatic cooking program, the analyzing unit 300 may automatically cook the food F in optimal cooking conditions and respond flexibly according to the cooking state of the food F and thus may cook the food F properly.

The food analysis apparatus according to one embodiment of the present invention may further include an adjuster (not illustrated) for controlling the operation of the cooking appliance 1 and a robot controller (not illustrated) which is mechanically connected to the adjuster and configured to manipulate the adjuster by operation control of the analyzing unit 300. In this case, the analyzing unit 300 may automatically control operation of the robot controller using the automatic cooking program.

The adjuster may be installed in a state of being exposed outside the cooking appliance 1, and a rotatable knob, a pressable button, or the like may be used for the adjuster, but the position and form of the adjuster may be changed in various ways as necessary.

The robot controller may be electrically connected (via a wire or wirelessly) to the analyzing unit 300 for operation of the robot controller to be controlled and may be installed in a state of being attached to an outer portion of the cooking appliance 1 or the adjuster. To this end, the robot controller may have a structure and operation method that allow the robot controller to rotate or press the adjuster, but the structure and operation method of the robot controller may be changed in various ways as necessary.

The food analysis apparatus according to one embodiment of the present invention may further include a communication unit 800 which is electrically connected to the analyzing unit 300 to send the analyzed molecular information to a server 50 at a remote place. The server 50 may send the molecular information of the food F sent from the communication unit 800 to a user terminal 60.

That is, since cooking information of the food is displayed through the user terminal 60, the user may cook while checking the cooking process of the food by visual inspection, and since the user may also check a recipe or the like for cooking the corresponding food by using the user terminal 60, the user may cook more conveniently.

Also, the food analysis apparatus according to one embodiment of the present invention may further include a cooling unit 400 for circulating a refrigerant W (water, air, etc.) throughout the inside of the support parts 210. The cooling unit 400 may include a storage tank configured to accommodate the refrigerant W or receive the refrigerant W from the outside and a pump configured to pump the refrigerant W out of the storage tank.

Here, the cooling unit 400 may be electrically connected to the analyzing unit 300 for operation of the cooling unit 400 to be controlled and may be connected to the inside of the support part 210 by a cooling water circulation line 410. The refrigerant W delivered through the cooling water circulation line 410 may be added to the installation space 212 of the support part 210. Also, the cooling unit 400 may be installed outside or inside the cooking appliance 1, but the installation position of the cooling unit 400 may be changed in various ways as necessary.

In another form, a separate flow path (not illustrated) through which the refrigerant W may be circulated may be formed inside the support part 210, and the refrigerant W delivered through the cooling water circulation line 410 may cool the support part 210 while circulating through the flow path of the support part 210.

A heat-resistant material may be used for the cooling water circulation line 410, and the cooling water circulation line 410 may be divided into a supply-side circulation line for adding the refrigerant W into the support part 210 and a discharge-side circulation line for adding the refrigerant W discharged from inside the support part 210 to the cooling unit.

In the process of cooking the food F, the cooling unit 400 cools the inside of the support part 210 to a set temperature. In this way, the cooling unit 400 may protect the light emitting part 220 and the light receiving part 230 installed in the installation space 212 of the support part 210 from external heat.

Also, as in FIGS. 11 and 12, a refrigerant discharging part 214 for spraying the refrigerant W to an outer surface of the heat-resistant member 213 coupled to the through-hole 211 may be further provided at one side of the support part 210. The refrigerant discharging part 214 may be formed at one side of the support part 210 in which the through-hole 211 is formed, and an outlet for discharging the refrigerant W to the outside may be formed inside the refrigerant discharging part 214.

The outlet of the refrigerant discharging part 214 may have an inflow side that communicates with the installation space 212 of the support part 210 and an outflow side, which is opposite to the inflow side, that communicates with the outside of the support part 210. Here, the outflow side of the outlet may spray the refrigerant W toward the outer surface of the heat-resistant member 213 from one side (lower portion, etc.) of the through-hole 211, and the outflow side of the outlet may communicate with the outside while being directed toward the outer surface of the heat-resistant member 213.

Also, as in FIGS. 6 to 8, the food analysis apparatus according to one embodiment of the present invention may further include a filter unit 500 for selectively blocking light of a wavelength in a specific range that is incident on the light receiving part 230.

The filter unit 500 may include a first moving part 510 which is provided to be position-changeable in front of the light receiving part 230 and has one or more noise filters 511 provided in front of the light receiving part 230 or provided to avoid the front of the light receiving part 230 and a first driving part 520 which is electrically connected to the analyzing unit 300 and configured to change the position of the first moving part 510.

The first moving part 510 may be located in front of the light receiving part 230 in the installation space 212 of the support part 210. The position of the first moving part 510 may be changed in a horizontal direction or vertical direction by a driving force of the first driving part 520, but the moving direction of the first moving part 510 may be changed in various ways as necessary.

The noise filter 511 is for passing only the light L in a specific wavelength band. In the case where a plurality of noise filters 511 are applied to the first moving part 510, the noise filters 511 may be selectively placed in front of the light receiving part 230. Since the wavelength band of the light L that passes through the noise filter 511 varies according to the type of noise filter 511 located in front of the light receiving part 230, rays of light L in various wavelength bands may be selectively received.

For example, in the case where the first moving part 510 is caused to avoid the front of the light receiving part 230, the light L incident through the through-hole 211 may be received through the lens 231 without passing through the noise filter 511. On the other hand, in the case where the noise filter 511 is placed in front of the lens 231 of the light receiving part 230, the light L incident through the through-hole 211 may be received through the lens 231 through the noise filter 511.

That is, in the case where noise that interferes with analysis is generated by heat (radiant heat, convection heat, conductive heat, etc.) which is generated during cooking of the food F, since the noise filter 511 located in front of the light receiving part 230 filters only the light L having a wavelength that deviates from a specific wavelength range, the sensing performance of the light receiving part 230 may be improved, and since the noise filter 511 may be selectively placed, rays of light L in various wavelength bands may be selectively filtered.

The first driving part 520 is for moving the first moving part 510 to a position in front of the light receiving part 230 or a position avoiding the front of the light receiving part 230. A motor, a cylinder, or the like for transmitting a rotational force may be selectively used as the first driving part 520.

In the case where a motor is applied as the first driving part 520, a driving shaft of the first driving part 520 may be mechanically connected to the first moving part 510 by a power transmission member (a gear, a belt, etc., not illustrated). In the case where a cylinder is applied as the first driving part 520, a rod (not illustrated) that projects from and retracts into the first driving part 520 may be connected to one side of the first moving part 510.

Here, the first driving part 520 may be coupled to one side of the support part 210, but the installation position of the first driving part 520 may be changed in various ways as necessary, and various forms may be selectively used as necessary for the power transmission member connecting the first driving part 520 and the first moving part 510.

Also, as in FIGS. 9 and 10, the food analysis apparatus according to one embodiment of the present invention may further include a cover unit 600 provided at one side of the support part 210 and configured to cover or expose the outer surface of the heat-resistant member 213.

The cover unit 600 may include a second moving part 610 which is provided to be movable between a position for covering the outer surface of the heat-resistant member 213 and a position for exposing the outer surface of the heat-resistant member 213 and a second driving part 620 which is electrically connected to the analyzing unit 300 and configured to change the position of the second moving part 610.

The second moving part 610 may be selectively placed in front of the heat-resistant member 213, and in the case where the second moving part 610 is located in front of the heat-resistant member 213, the second moving part 610 may cover a front surface of the heat-resistant member 213 so that oil mist, smoke, steam, or the like generated during the process of cooking the food F is not attached to the front surface of the heat-resistant member 213.

For example, using the above-described manipulation part 310 of the analyzing unit 300, the second moving part 610 may be moved to a position in front of the heat-resistant member 213 or a position avoiding the front of the heat-resistant member 213. In a situation in which oil mist, smoke, steam, or the like is generated in large amounts in the process of cooking the food F, the second moving part 610 may be placed in front of the heat-resistant member 213 to prevent contaminants (stains, etc.) from being attached to the front surface of the heat-resistant member 213.

Also, as in FIG. 10, a rubbing member 611 for rubbing the front surface of the heat-resistant member 213 may be further coupled to one surface of the second moving part 610. A heat-resistant fabric material or the like may be used for the rubbing member 611, and the rubbing member 611 may move along with the second moving part 610 in a state of being in close contact with the front surface of the heat-resistant member 213 and may rub off the contaminants attached to the front surface of the heat-resistant member 213 in the process in which the second moving part 610 is moved.

That is, since the front surface of the heat-resistant member 213 is not contaminated, the light L irradiated from the light emitting part 220 may be accurately irradiated toward the food F through the heat-resistant member 213, and the light L reflected from the food F may be accurately received by the light receiving part 230 through the heat-resistant member 213, and thus the sensing performance of the measuring unit 200 may be maintained in an optimal state.

The second driving part 620 is for moving the second moving part 610 to a position in front of the heat-resistant member 213 or a position avoiding the front of the heat-resistant member 213. A motor, a cylinder, or the like for transmitting a rotational force may be selectively used as the second driving part 620.

In the case where a motor is applied as the second driving part 620, a driving shaft of the second driving part 620 may be mechanically connected to the second moving part 610 by a power transmission member (a gear, a belt, etc., not illustrated). In the case where a cylinder is applied as the second driving part 620, a rod that projects from and retracts into the second driving part 620 may be connected to one side of the second moving part 610.

Here, the second driving part 620 may be coupled to one side of the support part 210, but the installation position of the second driving part 620 may be changed in various ways as necessary, and various forms may be selectively used as necessary for the power transmission member connecting the second driving part 620 and the second moving part 610.

Also, as in FIG. 5, the food analysis apparatus according to one embodiment of the present invention may further include a weight sensing unit 700 which is provided at the upper portion of the tray 100 to measure the weight of the food F placed in the cooking region. A load sensor, such as a load cell, or a force sensor, etc. may be selectively used for the weight sensing unit 700.

The weight sensing unit 700 may be electrically connected to the analyzing unit 300 and may transmit the measured weight and weight change value data of the food F to the analyzing unit 300, and the weight and weight change values measured by the weight sensing unit 700 may be displayed to the outside through the analyzing unit 300. Here, the analyzing unit 300 may operate the apparatus to correspond to the weight change value of the food F and automatically cook the food with a set recipe.

Hereinafter, a food analysis apparatus according to another embodiment of the present invention will be described with reference to FIG. 14. The food analysis apparatus according to another embodiment of the present invention includes a cooking chamber 10 of a cooking appliance 1 (an oven or the like), a measuring unit 200, and an analyzing unit 300.

The cooking chamber 10 forms a cooking space of a certain area so that food F may be placed therein, and an installation region A is formed at an upper end of one side of the cooking chamber 10 so that a housing 900, which will be described below, may be coupled.

Here, a door part 20 is provided to be openable/closeable at one side (front or the like) of the cooking chamber 10. The door part 20 may have a handle provided to be gripped by a user's hand and may have a transparent display window provided to allow the user to check the inside of the cooking chamber 10 by visual inspection.

Also, a heating part 30 for applying heat to the food F may be provided at an upper portion of the cooking chamber 10, the heating part 30 may have a structure that is heated by power transmitted from the outside, and an air blowing part for blowing heated air toward the cooking chamber 10 may be provided at an upper portion of the heating part 30.

In addition, a discharge part for discharging air to the outside may be provided at one side of the cooking chamber 10, an air blowing part for discharging an odor or the like generated during cooking to the outside may be provided in the discharge part, and a lighting part may be provided inside the cooking chamber 10 to be turned on in an operational situation such as when cooking is performed or when opening of the door part 20 is sensed.

Further, a mounting part 40 for placing a tray 100, which will be described below, at a certain height may be provided at both sides of the cooking chamber 10. A plurality of mounting parts 40 may be arranged in a state of being spaced apart from each other in the vertical direction to allow a height for mounting the tray 100 to be selected.

The measuring unit 200 is for irradiating light L to be inclined downward toward the food F placed in a cooking region and then receiving the reflected light to sense spectral characteristics thereof. The measuring unit 200 is coupled to the installation region A of the cooking chamber 10. The installation region A may be formed at an inlet-side upper end of the cooking chamber, but the position of the installation region A may be changed in various ways as necessary.

The measuring unit 200 according to another embodiment of the present invention may include the housing 900 which is coupled to the installation region A and has a sensing surface 902 formed to be inclined downward at one side, a first through-hole 910 provided to be inclined downward in the sensing surface 902, a second through-hole 920 provided to be inclined downward in the sensing surface 902, a light emitting part 220 which is provided in the housing 900 and configured to irradiate light to be inclined downward toward the food F through the first through-hole 910, and a light receiving part 230 which is provided in the housing 900 and configured to sense spectral characteristics of the light L that is incident to be inclined upward through the second through-hole 920.

The housing 900 may have an upper end coupled to the installation region A, and an installation space 901 for installing the light emitting part 220 and the light receiving part 230 may be formed in the housing 900. The housing 900 may be manufactured using a heat-resistant material to prevent the housing 900 from being deformed by heat transmitted from the outside during cooking.

Also, a heat-resistant member 930 for passing the light L and blocking heat may be further coupled to the first through-hole 910 and the second through-hole 920. The heat-resistant member 930 may be manufactured using a heat-resistant material to prevent the heat-resistant member 930 from being deformed by heat transmitted from the outside during cooking, or various other materials may be selectively used as necessary for the heat-resistant member 930.

The light emitting part 220 is a component for irradiating the food F seated in the cooking chamber 10 with the light L. The light emitting part 220 may be installed in the installation space 901 of the housing 900 and may be electrically connected (via a wire or wirelessly) to the analyzing unit 300, which will be described below, for operation of the light emitting part 220 to be controlled. Here, one or more lamps 221 for irradiating the light L to be inclined downward toward the cooking region through the first through-hole 910 may be installed at one side of the light emitting part 220. An LED may be used for the lamp 221, but various other forms may be selectively used as necessary for the lamp 221.

The light L irradiated from the lamp 221 of the light emitting part 220 may be irradiated to be inclined downward toward the food F placed in the cooking region through the heat-resistant member 213, and the light L reflected from the food F may be incident to be inclined upward through the light receiving part 230. Here, the light L irradiated from the lamp 221 of the light emitting part 220 may be irradiated with a certain area toward the cooking region, and the area, angle, illuminance, or the like with which the light L is irradiated may vary. The light L irradiated from the lamp 221 may be irradiated toward the entire region of the cooking region or irradiated toward a partial region of the cooking region.

The light receiving part 230 is a component for receiving the light L reflected from the food F. The light receiving part 230 may be installed in the installation space 901 of the housing 900 and may be electrically connected (via a wire or wirelessly) to the analyzing unit 300, which will be described below, for operation of the light receiving part 230 to be controlled.

Here, a lens 231 for receiving the light L incident through the second through-hole 920 may be installed at one side of the light receiving part 230. An image sensor such as a CMOS or a CCD may be selectively used for the light receiving part 230, but various other sensing methods may be used as necessary for the light receiving part 230.

In the case where the light L reflected from the food F is received through the lens 231, the light receiving part 230 senses spectral characteristics of the received light and transmits a sensing signal to the analyzing unit 300 which will be described below. Here, the analyzing unit 300 analyzes the spectral characteristics transmitted from the light receiving part 230 to detect molecular information of the food F.

For example, the light emitting part 220 and the light receiving part 230 may be installed in vertical and horizontal directions of the installation space 901, and the first through-hole 910 and the second through-hole 920 may be installed at a height that corresponds to one side of the light emitting part 220 and the light receiving part 230. The installation positions of the light emitting part 220, the light receiving part 230, the first through-hole 910, and the second through-hole 920 may be changed in various ways as necessary.

The analyzing unit 300 may analyze the spectral characteristics of the light L, which are transmitted from the measuring unit 200, to detect molecular information (moisture content, a protein/fat/collagen composition ratio, the degree of ripening, the degree of Maillard reaction, a change in characteristics of muscle fibers, etc.) of the food F and may control operation of the heating part 30 of the cooking appliance 1, the air blowing part, the measuring unit 200, and the like. Here, a power supply unit 70 for supplying power and a manipulation part (not illustrated) configured to allow manipulation by the user may be electrically connected to the analyzing unit 300.

Also, the analyzing unit 300 may be electrically connected to the light emitting part 220 and the light receiving part 230 by a power cable, the power cable connected to the analyzing unit 300 may be connected to each of the light emitting part 220 and the light receiving part 230 through the inside of the housing 900, and the manipulation part may be connected via a wire or wirelessly to the analyzing unit 300.

In the case where a wired manipulation method is applied to the manipulation part, the manipulation part and the analyzing unit 300 may be connected by a connection line (a cable, etc.). In this case, the manipulation part may be installed in a state of being coupled to an outer portion of the cooking appliance 1 or installed in a state of being connected to the cooking appliance 1 by the connection line.

On the other hand, in the case where a wireless manipulation method is applied to the manipulation part, a near-field communication method such as RFID, Bluetooth, and Wi-Fi may be used for connecting the manipulation part and the analyzing unit 300.

Also, a manipulation switch (not illustrated) for allowing the user to control the operation of the cooking appliance 1 and a display part (not illustrated) for displaying various pieces of information (cooking time, cooking intensity, molecular information, etc.) of the cooking appliance 1 to the outside may be provided at the manipulation part, and in the case where a wireless manipulation method is applied to the manipulation part, a battery module (not illustrated) which is replaceable or rechargeable may be provided in the manipulation part.

The analyzing unit 300 may detect molecular information (moisture content, a protein/fat/collagen composition ratio, the degree of ripening, the degree of Maillard reaction, a change in characteristics of muscle fibers, etc.) of the food F and display a cooking state of the food F to the outside in a process in which the cooking appliance 1 operates, and using the detected molecular information, the analyzing unit 300 may automatically cook the corresponding food F with a set recipe.

Also, the food analysis apparatus according to another embodiment of the present invention may further include a communication unit (not illustrated) which is electrically connected to the analyzing unit 300 to send the analyzed molecular information to a server (not illustrated) at a remote place. The server may send the molecular information of the food F sent from the communication unit to a user terminal (not illustrated).

That is, since cooking information of the food is displayed through the user terminal, the user may cook while checking the cooking process of the food F by visual inspection, and since the user may also check a recipe or the like for cooking the corresponding food F by using the user terminal, the user may cook more conveniently.

Also, the food analysis apparatus according to another embodiment of the present invention may further include a cooling unit 400 for circulating a refrigerant W (water, air, etc.) throughout the inside of the housing 900. The cooling unit 400 may include a storage tank configured to accommodate the refrigerant W or receive the refrigerant W from the outside and a pump configured to pump the refrigerant W out of the storage tank.

Here, the cooling unit 400 may be electrically connected to the analyzing unit 300 for operation of the cooling unit 400 to be controlled and may be connected to the inside of the housing 900 by a cooling water circulation line 410. The refrigerant W delivered through the cooling water circulation line 410 may be added to the installation space 901 of the housing 900. Also, the cooling unit 400 may be installed outside or inside the cooking appliance 1, but the installation position of the cooling unit 400 may be changed in various ways as necessary.

In another form, a separate flow path (not illustrated) through which the refrigerant W may be circulated may be formed inside the housing 900, and the refrigerant W delivered through the cooling water circulation line 410 may cool the housing 900 while circulating through the flow path of the housing 900.

A heat-resistant material may be used for the cooling water circulation line 410, and the cooling water circulation line 410 may be divided into a supply-side circulation line for adding the refrigerant W into the housing 900 and a discharge-side circulation line for adding the refrigerant W discharged from inside the housing 900 to the cooling unit 400.

In the process of cooking the food F, the cooling unit 400 cools the inside of the housing 900 to a set temperature. In this way, the cooling unit 400 may protect the light emitting part 220 and the light receiving part 230 installed in the installation space 901 of the housing 900 from external heat.

Also, a refrigerant discharging part (not illustrated) for spraying the refrigerant W to an outer surface of the heat-resistant member 930 coupled to the first through-hole 910 and the second through-hole 920 may be further provided at one side of the housing 900. The refrigerant discharging part may be formed at the sensing surface 902 of the housing 900 in which the first through-hole 910 and the second through-hole 920 are formed, and an outlet for discharging the refrigerant W to the outside may be formed inside the refrigerant discharging part.

The outlet of the refrigerant discharging part may have an inflow side that communicates with the installation space 901 of the housing 900 and an outflow side, which is opposite to the inflow side, that communicates with the outside of the housing 900. Here, the outflow side of the outlet may spray the refrigerant W toward the outer surface of the heat-resistant member 930 from one side (lower portion, etc.) of the first through-hole 910 and the second through-hole 920, and the outflow side of the outlet may communicate with the outside while being directed toward the outer surface of the heat-resistant member 930.

Also, the food analysis apparatus according to another embodiment of the present invention may further include a filter unit (not illustrated) for selectively blocking light of a wavelength in a specific range that is incident on the light receiving part 230.

The filter unit may include a first moving part (not illustrated) which is provided to be position-changeable in front of the light receiving part 230 and has one or more noise filters (not illustrated) provided in front of the light receiving part 230 or provided to avoid the front of the light receiving part 230 and a first driving part (not illustrated) which is electrically connected to the analyzing unit 300 and configured to change the position of the first moving part.

The first moving part may be located in front of the light receiving part 230 in the installation space 901 of the housing 900. The position of the first moving part may be changed in the horizontal direction or vertical direction by a driving force of the first driving part, but the moving direction of the first moving part may be changed in various ways as necessary.

The noise filter is for passing only the light L in a specific wavelength band. In the case where a plurality of noise filters are applied to the first moving part, the noise filters may be selectively placed in front of the light receiving part 230. Since the wavelength band of the light L that passes through the noise filter varies according to the type of noise filter located in front of the light receiving part 230, rays of light L in various wavelength bands may be selectively received.

For example, in the case where the first moving part is caused to avoid the front of the light receiving part 230, the light L incident through the second through-hole 920 may be received through the lens 231 without passing through the noise filter. On the other hand, in the case where the noise filter is placed in front of the lens 231 of the light receiving part 230, the light L incident through the second through-hole 920 may be received through the lens 231 through the corresponding noise filter.

That is, in the case where noise that interferes with analysis is generated by heat (radiant heat, convection heat, conductive heat, etc.) which is generated during cooking of the food F, since the noise filter located in front of the light receiving part 230 filters only the light L having a wavelength that deviates from a specific wavelength range, the sensing performance of the light receiving part 230 may be improved, and since the noise filter may be selectively placed, rays of light L in various wavelength bands may be selectively filtered.

The first driving part is for moving the first moving part to a position in front of the light receiving part 230 or a position avoiding the front of the light receiving part 230. A motor, a cylinder, or the like for transmitting a rotational force may be selectively used as the first driving part.

In the case where a motor is applied as the first driving part, a driving shaft of the first driving part may be mechanically connected to the first moving part by a power transmission member (a gear, a belt, etc., not illustrated). In the case where a cylinder is applied as the first driving part, a rod (not illustrated) that projects from and retracts into the first driving part may be connected to one side of the first moving part.

Here, the first driving part may be coupled to one side of the housing 900, but the installation position of the first driving part may be changed in various ways as necessary, and various forms may be selectively used as necessary for the power transmission member connecting the first driving part and the first moving part.

Also, the food analysis apparatus according to another embodiment of the present invention may further include a cover unit (not illustrated) provided at one side of the housing 900 and configured to cover or expose the outer surface of the heat-resistant member 930.

The cover unit may include a second moving part (not illustrated) which is provided to be movable between a position for covering the outer surface of the heat-resistant member 930 and a position for exposing the outer surface of the heat-resistant member 930 and a second driving part (not illustrated) which is electrically connected to the analyzing unit 300 and configured to change the position of the second moving part.

The second moving part may be selectively placed in front of the heat-resistant member 930, and in the case where the second moving part is located in front of the heat-resistant member 930, the second moving part may cover a front surface of the heat-resistant member 930 so that oil mist, smoke, steam, or the like generated during the process of cooking the food F is not attached to the front surface of the heat-resistant member 930.

For example, using the above-described manipulation part of the analyzing unit 300, the second moving part may be moved to a position in front of the heat-resistant member 930 or a position avoiding the front of the heat-resistant member 930. In a situation in which oil mist, smoke, steam, or the like is generated in large amounts in the process of cooking the food F, the second moving part may be placed in front of the heat-resistant member 930 to prevent contaminants (stains, etc.) from being attached to the front surface of the heat-resistant member 930.

Also, a rubbing member (not illustrated) for rubbing the front surface of the heat-resistant member 930 may be further coupled to one surface of the second moving part. A heat-resistant fabric material or the like may be used for the rubbing member, and the rubbing member may move along with the second moving part in a state of being in close contact with the front surface of the heat-resistant member 930 and may rub off the contaminants attached to the front surface of the heat-resistant member 930 in the process in which the second moving part is moved.

That is, since the front surface of the heat-resistant member 930 is not contaminated, the light L irradiated from the light emitting part 220 may be accurately irradiated toward the food F through the heat-resistant member 930, and the light L reflected from the food F may be accurately received by the light receiving part 230 through the heat-resistant member 930, and thus the sensing performance of the measuring unit 200 may be maintained in an optimal state.

The second driving part is for moving the second moving part to a position in front of the heat-resistant member 930 or a position avoiding the front of the heat-resistant member 930. A motor, a cylinder, or the like for transmitting a rotational force may be selectively used as the second driving part.

In the case where a motor is applied as the second driving part, a driving shaft of the second driving part may be mechanically connected to the second moving part by a power transmission member (a gear, a belt, etc., not illustrated). In the case where a cylinder is applied as the second driving part, a rod that projects from and retracts into the second driving part may be connected to one side of the second moving part.

Here, the second driving part may be coupled to one side of the housing 900, but the installation position of the second driving part may be changed in various ways as necessary, and various forms may be selectively used as necessary for the power transmission member connecting the second driving part and the second moving part.

Consequently, according to the present invention, since it is possible to analyze molecular information of food in real time in a cooking process, the corresponding food F may be cooked with an optimal recipe, and since the measuring unit 200 is located at a position spaced apart from an installation region of the heating part 30, the measuring unit 200 may be easily cleaned without interference between the measuring unit 200 and the heating part 30, and the risk of accidents while cleaning the measuring unit 200 may be reduced.

Also, according to the present invention, since it is easy to secure an installation space for the heating part 30, degradation of heating performance may be prevented. Since application to various cooking appliances is possible, a general-purpose use is possible. Since it is possible to prevent attachment of foreign matter to the measuring unit 200 and remove foreign matter attached to the measuring unit 200 during the cooking process, food analysis performance may be maintained in an optimal state.

Specific embodiments relating to the food analysis apparatus according to the present invention have been described above, but it should be apparent that various modifications are possible within the scope not departing from the scope of the present invention.

Therefore, the scope of the present invention should not be defined as being limited to the embodiments described herein and should be defined by the attached claims and their equivalents.

That is, the embodiments described herein should be understood as being illustrative, instead of limiting, in all aspects. The scope of the present invention is shown by the attached claims rather than by the detailed description above, and all changes or modifications derived from the meaning and scope of the claims and their equivalents should be construed as belonging to the scope of the present invention.

MODES OF THE INVENTION

The modes of the invention have been described above in describing the best mode of the invention.

INDUSTRIAL APPLICABILITY

The present invention makes it possible to analyze molecular information of food during a cooking process. In this way, the present invention has industrial applicability.

The invention claimed is:

1. A food analysis apparatus comprising:
    a cooking chamber provided in a cooking appliance;
    a measuring unit configured to irradiate food placed in a cooking region inside the cooking chamber with light and then sense spectral characteristics of reflected light; and
    an analyzing unit configured to analyze the spectral characteristics transmitted from the measuring unit to detect molecular information of the food;
    wherein the measuring unit includes:
    a pair of support parts each having a through-hole formed at one side;
    a light emitting part which is provided in one of the pair of support parts and configured to irradiate the food placed in the cooking region with light through the through-hole; and
    a light receiving part which is provided in the other one of the pair of support parts and configured to sense spectral characteristics of light that is incident through the through-hole and transmit the spectral characteristics to the analyzing unit.

2. The food analysis apparatus of claim 1, further comprising a tray which is mounted in the cooking chamber and has the cooking region formed at an upper portion,
    wherein the measuring unit is provided at the upper portion of the tray.

3. The food analysis apparatus of claim 1, further comprising a mounting frame which is mounted in the cooking chamber and has a hollow vertically passing therethrough,
    wherein the measuring unit is provided on the mounting frame.

4. The food analysis apparatus of claim 1, wherein the measuring unit includes:
    a support part which has a pair of through-holes provided at one side;
    a light emitting part which is provided in the support part and configured to irradiate the food placed in the cooking region with light through one of the pair of through-holes; and a light receiving part which is provided in the support part and configured to sense spectral characteristics of light that is incident through the other one of the pair of through-holes and transmit the spectral characteristics to the analyzing unit.

5. The food analysis apparatus of claim 4, further comprising a filter unit configured to selectively block light of a wavelength in a specific range that is incident on the light receiving part,
wherein the filter unit further includes a first moving part which is provided to be position-changeable in front of the light receiving part and has one or more noise filters provided in front of the light receiving part or provided to avoid the front of the light receiving part and a first driving part which is electrically connected to the analyzing unit and configured to change the position of the first moving part.

6. The food analysis apparatus of claim 4, wherein a heat-resistant member for passing light and blocking heat is further coupled to the through-hole.

7. The food analysis apparatus of claim 6, further comprising:
a power supply unit electrically connected to the measuring unit; and
a cooling unit configured to circulate a refrigerant throughout the inside of the support part.

8. The food analysis apparatus of claim 7, further comprising a refrigerant discharging part which is formed to be penetrated at an outer portion of the support part and allows the refrigerant to be sprayed to an outer surface of the heat-resistant member.

9. The food analysis apparatus of claim 6, further comprising a cover unit provided to be position-changeable at one side of the support part,
wherein the cover unit further includes a second moving part which is provided to be movable between a position for covering the outer surface of the heat-resistant member and a position for exposing the outer surface of the heat-resistant member and a second driving part which is electrically connected to the analyzing unit and configured to change the position of the second moving part.

10. The food analysis apparatus of claim 2, further comprising a weight sensing unit which is provided at the upper portion of the tray and configured to measure a weight of the food placed in the cooking region,
wherein the weight sensing unit is electrically connected to the analyzing unit and transmits the measured weight of the food to the analyzing unit.

11. The food analysis apparatus of claim 1, wherein the analyzing unit displays a cooking state of the food to the outside.

12. The food analysis apparatus of claim 1, wherein the analyzing unit automatically controls operation of the cooking appliance according to the detected molecular information.

13. The food analysis apparatus of claim 12, further comprising:
an adjuster configured to control the operation of the cooking appliance; and
a robot controller which is mechanically connected to the adjuster and configured to manipulate the adjuster by operation control of the analyzing unit,
wherein the analyzing unit automatically controls operation of the robot controller.

14. The food analysis apparatus of claim 12, wherein the analyzing unit controls the cooking appliance by a wired or wireless communication method.

15. A food analysis apparatus comprising:
a cooking chamber which is provided in a cooking appliance and has an installation region provided at an upper end of one side;
a measuring unit which is coupled to the installation region and configured to irradiate light to be inclined downward toward food placed in the cooking chamber and then sense spectral characteristics of reflected light; and
an analyzing unit which is electrically connected to the measuring unit and configured to analyze the spectral characteristics transmitted from the measuring unit to detect molecular information of the food,
wherein the measuring unit includes:
a pair of support parts each having a through-hole formed at one side;
a light emitting part which is provided in one of the pair of support parts and configured to irradiate the food placed in the cooking region with light through the through-hole; and
a light receiving part which is provided in the other one of the pair of support parts and configured to sense spectral characteristics of light that is incident through the through-hole and transmit the spectral characteristics to the analyzing unit.

16. The food analysis apparatus of claim 15, wherein the measuring unit includes:
a housing which is coupled to the installation region and has a sensing surface formed to be inclined downward at one side;
a first through-hole provided to be inclined downward in the sensing surface;
a second through-hole provided to be inclined downward in the sensing surface;
a light emitting part which is provided in the housing and configured to irradiate light to be inclined downward toward the food through the first through-hole; and
a light receiving part which is provided in the housing and configured to sense spectral characteristics of light that is incident to be inclined upward through the second through-hole.

17. The food analysis apparatus of claim 16, further comprising:
a power supply unit electrically connected to the measuring unit; and
a cooling unit configured to circulate a refrigerant throughout the inside of the housing.

* * * * *